United States Patent [19]

Cordier

[11] Patent Number: 4,987,263

[45] Date of Patent: Jan. 22, 1991

[54] PREPARATION OF 2-METHYLPENTADIAMINE

[75] Inventor: Georges Cordier, Francheville, France

[73] Assignee: Rhone-Poulenc Chimie, Courbevoie, France

[21] Appl. No.: 231,440

[22] Filed: Aug. 12, 1988

[30] Foreign Application Priority Data

Aug. 12, 1987 [FR] France ................. 87 11263

[51] Int. Cl.$^5$ ................. C07C 209/00; C07D 211/12
[52] U.S. Cl. ................. 564/491; 546/184
[58] Field of Search ................. 564/491, 511; 546/184

[56] References Cited

U.S. PATENT DOCUMENTS

| | | | |
|---|---|---|---|
| 3,953,511 | 4/1976 | Frech et al. | 260/583 K |
| 4,003,933 | 1/1977 | Drake | 260/583 K |
| 4,429,159 | 1/1984 | Cutchens et al. | 564/492 |

FOREIGN PATENT DOCUMENTS 0048951  3/1985  Japan .
0245678  8/1947  Switzerland .

*Primary Examiner*—Glennon H. Hollrah
*Assistant Examiner*—Peter G. O'Sullivan
*Attorney, Agent, or Firm*—Burns, Doane, Swecker & Mathis

[57] ABSTRACT

2-Methylpentanediamine is prepared by selectively liquid-phase hydrogenating a minimum concentration 2-methylglutaronitrile, initially nonammoniacal basic reaction medium in the presence of a catalytically effective amount of a Raney nickel-based catalyst, at a temperature of from 40° to 150° C., at a total pressure of less than 40 bars, and said reaction medium containing not more than 10% by weight of water.

15 Claims, No Drawings

4,987,263

PREPARATION OF 2-METHYLPENTADIAMINE

BACKGROUND OF THE INVENTION

1. Field of the Invention:

The present invention relates to the preparation of 2-methylpentanediamine by hydrogenation of 2-methylglutaronitrile.

2. Description of the Prior Art:

Variable but relatively large amounts of 2-methylglutaronitrile are produced in the course of industrial manufacture of adiponitrile by hydrocyanation of 3-pentenenitrile. This by-product can be destroyed, and this, quite obviously, is unsatisfactory from an economic standpoint. It may also be reclaimed, not as such, but after conversion into a useful product. Among the reclaiming processes which appear to be the most promising, there may be mentioned the conversion of 2-methylglutaronitrile into the corresponding isocyanate (2-methylpentane diisocyanate) and, if appropriate, into its derivatives such as biuret and the triisocyanate. This conversion is carried out in two successive operations, namely: hydrogenation of 2-methylglutaronitrile into 2-methylpentanediamine, followed by the phosgenation of the 2-methylpentanediamine into diisocyanate, according to the techniques described, for example, in U.S. Pat. No. 3,631,198. Another possible way of reclaiming 2-methylglutaronitrile entails converting it into 2-methylpentanediamine, which can be employed in the production of specialty polyamides.

In both such cases, it is important to obtain high selectivity and space/time yield during the hydrogenation, to ensure the best possible reclamation of 2-methylglutaronitrile.

Further, the hydrogenation of saturated, alkyl-substituted aliphatic dinitriles is a reaction which has prompted a great number of previous studies. Thus, for example, in published German Patent Application No. 1,543,793, 2-methylglutaronitrile is described as being hydrogenated at 100° C. and at 300 atmospheres in the presence of a Raney cobalt-based catalyst, in absolute alcohol, also in the presence of anhydrous ammonia, to produce 2-methylpentanediamine admixed with 3-methylpiperidine and polymers of unidentified nature, in the following yields, respectively: 80, 18 and 2 (in percent), no mention being made of the hydrogenation time.

In published French Patent Application No. 2,306,202, 2-methylglutaronitrile is described as being hydrogenated at 110° C. and at 400 atmospheres in the presence of cobalt in liquid ammonia, the 2-methylglutaronitrile being continuously charged, hydrogen being recycled, and the reaction mixture being withdrawn continuously. The average composition of such mixture is as follows: 90.9% of 2-methylpentanediamine, 8.2% of 3-methylpiperidine and on the order of 2% of heavy products (cf. Example 1 designated "comparative example" of said application). Example 2 of the same application shows that, all other conditions being equal, hydrogenation of 2-methylglutaronitrile carried out in the presence of a nickel-based catalyst does not permit 2-methylpentanediamine to be selectively obtained since, on the contrary, the reaction mixture thus obtained contains 90.1% of 3-methylpiperidine versus 3.9% of 2-methylpentanediamine and from 6 to 8% of heavy materials. Example 6 of this same application shows, moreover, that when the hydrogenation of 2-methylglutaronitrile is carried out noncontinuously, in the absence of liquid ammonia, at 140° C. and at 300 atmospheres in the presence of nickel in an ethanolic medium containing sodium hydroxide, 2-methylpentanediamine is produced after 2 hours, mixed in particular with 3-methylpiperidine, with a selectivity of only 29.4% (molar).

Furthermore, in U.S. Pat. No. 3,953,511 a multistage process is described, in which the hydrogenation of 2-methylglutaronitrile, which constitutes the second stage of the process, is carried out in the presence of Raney nickel at a temperature of 120° to 140° C. and at a hydrogen pressure of at least 42 kg/cm$^2$, to produce 2-methylpentanediamine, the reaction medium comprising an alcoholic solvent which contains ammonia.

However, the selectivity for 2-methylpentanediamine is not satisfactory: it remains between approximately 55 and 60%.

To summarize, none of the previously known processes is fully satisfactory insofar as each exhibits at least one of the following disadvantages:

(1) the need to operate at very high pressure to obtain a worthwhile result using a Raney cobalt-based catalyst;

(2) the lack of selectivity for 2-methylpentanediamine, either to the advantage of heavier products, or to the advantage of another unwanted compound, in this case (3-methylpiperidine); and (3) the lack of efficiency of the various proposed techniques, particularly due to the long processing times required.

Cf. U.S. Pat. No. 3,322,815 and Swiss Patent No. 245,678.

SUMMARY OF THE INVENTION

Accordingly, a major object of the present invention is the provision of an improved process for the hydrogenation of 2-methylglutaronitrile to selectively produce 2-methylpentanediamine, and which improved process conspicuously ameliorates those disadvantages and drawbacks to date characterizing the state of this art.

Briefly, the present invention features a process for the preparation of 2-methylpentanediamine by liquid-phase hydrogenation of 2-methylglutaronitrile in the presence of a Raney nickel-based catalyst, in an initially nonammoniacal basic medium, and wherein the hydrogenation reaction is carried out at a temperature of from 40° to 150° C., at a total pressure of less than 40 bars, in a reaction medium containing not more than 10% by weight of water, with the concentration of 2-methylglutaronitrile in the reaction medium being as low as possible.

DETAILED DESCRIPTION OF THE PREFERRED EMBODIMENTS OF THE INVENTION

More particularly according to the present invention, the subject process is carried out in liquid phase, in the presence of a Raney nickel-based catalyst.

Such reaction is between the liquid 2-methylglutaronitrile introduced, if appropriate, in a solvent or diluent, and gaseous hydrogen under pressure, in the presence of a catalyst which is typically solid. It is therefore important that it be conducted in an apparatus, the design and method of operation of which promote contact between these 3 phases.

By "Raney nickel-based catalyst" (or one of the Raney type) is intended essentially particulate and high surface area, catalytic forms of nickel, doped or stabilized, if appropriate, with chromium and with iron, for example. These particular catalytic forms are generally obtained in a manner known per se, from an alloy containing nickel, one or more dopant(s) if appropriate, and aluminum, the nickel being present in the "dissolved" state in the aluminum. These alloys are then subjected to an alkaline washing in order to remove most of the aluminum contained therein. These alloys can nevertheless contain up to approximately 20 to 30% by weight of aluminum, after treatment.

The citations below are representative of the general knowledge on the subject and especially with regard to the various preparative techniques:

(i) Chemical Technology Review No. 94, *Hydrogenation Catalysts*. R. J. Peterson/Noyes Data Corp. 1977, "Preparation of Nickel Hydrogenation Catalyst", pages 3-10;

(ii) R. L. Augustine, *Catalytic Hydrogenation*, Marcel Dekker Inc. NY 1965, pages 26-32, and appendices pages 147-149.

Many Raney nickel-based catalysts are commercial materials and are suitable for carrying out the process according to the invention.

The hydrogenation reaction is carried out in an initially nonammoniacal basic medium.

The initial basicity of the medium is provided by the presence of a hydroxide of an alkali metal such as sodium, potassium or lithium, or of a quaternary ammonium hydroxide, with the exclusion of ammonia or of ammoniacal solutions. Naturally, as is well known to this art, ammonia is formed during the hydrogenation in question and can be at least partially converted into aqueous ammonia in the presence of water. However, according to the present invention, it is essential to not carry out the hydrogenation reaction in the presence of an additional amount of ammonia or of aqueous ammonia. This is what is intended by the proviso that the basic medium under consideration is "initially nonammoniacal".

By "quaternary ammonium hydroxide" are intended the hydroxy compounds in which the associated cation corresponds to any one of the formulae (I) to (III) below:

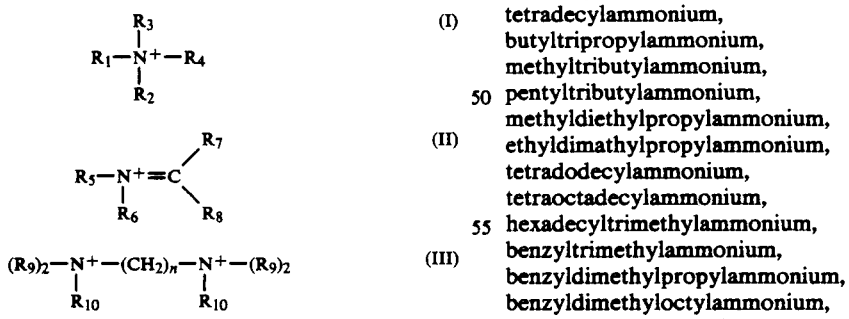

t,80
in which:

$R_1$, $R_2$, $R_3$ and $R_4$, which may be identical or different, are each a linear or branched chain alkyl radical containing from 1 to 16 carbon atoms, optionally substituted by a phenyl, hydroxyl, halogen, nitro, alkoxy or alkoxycarbonyl group;

a linear or branched chain alkenyl radical containing from 2 to 12 carbon atoms, preferably from 4 to 8 carbon atoms;

or an aryl radical containing from 6 to 10 carbon atoms, optionally substituted by one or more alkyl radicals containing from 1 to 4 carbon atoms, or by an alkoxy, alkoxycarbonyl or halogen group, with the proviso that two of said radicals $R_1$ to $R_4$ may together form a linear or branched chain alkylene, alkenylene or alkadienylene radical containing from 3 to 6 carbon atoms;

$R_5$, $R_6$, $R_7$ and $R_8$, which may be identical or different, are each a linear or branched chain alkyl radical containing from 1 to 4 carbon atoms; with the proviso that the radicals $R_7$ and $R_8$ may together form an alkylene radical containing from 3 to 6 carbon atoms; and with the further proviso that the radicals $R_6$ and $R_7$ or $R_6$ and $R_8$ may together form an alkylene, alkenylene or alkadienylene radical containing 4 carbon atoms and constituting a nitrogenous heterocyclic ring with the nitrogen atom;

$R_9$ is a linear or branched chain alkyl radical containing from 1 to 4 carbon atoms or a phenyl radical;

$R_{10}$ is a linear or branched chain alkyl radical containing from 1 to 4 carbon atoms, the same or different from $R_9$;

or a linear or branched chain alkenyl radical containing from 2 to 12 carbon atoms, preferably from 4 to 8 carbon atoms; and n is an integer greater than or equal to 1 and less than or equal to 10 and preferably less than or equal to 6.

Exemplary of quaternary onium cations corresponding to formula I, the following cations are representative:

tetramethylammonium,
triethylmethylammonium,
tributylmethylammonium,
trimethyl(n-propyl)ammonium,
tetraethylammonium,
tetrabutylammonium,
dodecyltrimethylammonium,
methyltrioctylammonium,
heptyltributylammonium,
tetrapropylammonium,
tetrapentylammonium,
tetrahexylammonium,
tetraheptylammonium,
tetraoctylammonium,
tetradecylammonium,
butyltripropylammonium,
methyltributylammonium,
pentyltributylammonium,
methyldiethylpropylammonium,
ethyldimathylpropylammonium,
tetradodecylammonium,
tetraoctadecylammonium,
hexadecyltrimethylammonium,
benzyltrimethylammonium,
benzyldimethylpropylammonium,
benzyldimethyloctylammonium,
benzyltributylammonium,
benzyltriethylammonium,
phenyltrimethylammonium,
benzyldimethyltetradecylammonium,
benzyldimethylhexadecylammonium,
dimethyldiphenylammonium,
methyltriphenylammonium,
N,N-dimethyltetramethyleneammonium,
N,N-diethyltetramethyleneammonium.

Exemplary cations corresponding to formula II, the following cations are representative:

N-methylpyridinium,
N-ethylpyridinium,
N-hexadecylpyridinium,
N-methylpicolinium.

And exemplary cations corresponding to formula III, the following cations are representative:

1,2-bis(trimethylammonium)ethane,
1,3-bis(trimethylammonium)propane,
1,4-bis(trimethylammonium)butane,
1,3-bis(trimethylammonium)butane.

Among these quaternary ammonium hydroxides, preferred are those in which the associated cation corresponds to formula (I) above, in which at least any three of the radicals $R_1$ to $R_4$ are identical and are alkyl radicals containing from 1 to 10 carbon atoms, and preferably from 1 to 4 carbon atoms, the other of such radicals being alkyl, aryl or aralkyl radicals which contain not more than 10 carbon atoms.

By way of example of such cations, the following are representative:

tetramethylammonium,
tetraethylammonium,
benzyltrimethylammonium,
phenyltrimethylammonium.

Among the alkali metal hydroxides, preferred are sodium hydroxide and potassium hydroxide.

The basic reaction medium may include an exogenous diluent and more particularly an alkanol containing from 1 to 12 carbon atoms. An alkanol containing from 1 to 4 carbon atoms, and more particularly ethanol or isopropanol, is preferably used.

The reaction medium may contain no exogenous diluent; it will then contain an endogenous diluent which is 2-methylpentanediamine mixed, if appropriate, with 3-methylpiperidine. The basic agent (the hydroxide referred to above) will then be dissolved or dispersed in the diluent.

The concentrations of the basic agent and of the Raney nickel-based catalyst in the reaction medium may vary over wide limits.

The catalyst (expressed as nickel) may constitute from 0.5 to 50% by weight of the diluent (endogenous or exogenous), and it preferably constitutes from 1 to 15% by weight of the diluent.

The alkali metal or quaternary ammonium hydroxide may constitute from 0.5 to 50% (molar) in relation to the nickel and, preferably, it constitutes from 2 to 35% (molar) in relation to the nickel.

The hydrogenation reaction is carried out at a temperature of from 40° to 150° C.; below 40° C., the reaction rate is insufficient, and above 150° C. the formation of heavy products becomes unacceptable. This temperature advantageously ranges from 60° to 110° C.

The total pressure, measured at the reaction temperature, is below 40 bars. It is advantageously 5 bars or above, and, preferably, ranges from 5 to 25 bars.

When carrying out the process according to the invention, it is essential to limit the water content of the reaction medium such that it does not exceed 10% by weight and is preferably below or equal to 4% by weight of said medium.

As indicated above, when the process according to the invention is carried out it is essential that the concentration of 2-methylglutaronitrile in the reaction mixture be as low as possible.

Although, in principle, it is possible to produce the desired compound in a selective manner by employing an operating procedure entailing successive charges, this noncontinuous method makes it necessary to utilize a high dilution of 2-methylglutaronitrile, namely, an initial concentration of this starting material which is below 20% by weight and, preferably, below 10% by weight of the reaction medium.

In an advantageous embodiment of the present invention, the operation is carried out according to an at least semicontinuous method, in the sense that 2-methylglutaronitrile, taken either alone or diluted in a diluent specified earlier, is introduced such that at any time during the reaction the hydrogen consumption is 4 moles per mole of 2-methylglutaronitrile employed, with a tolerance of 3% in excess or in deficiency, and that the concentration of 2-methylglutaronitrile in the reaction medium, monitored by analysis, is below 0.1% by weight.

For a proper carrying out of the process of the present invention, the total amount of 2-methylglutaronitrile to be hydrogenated will be at least equal to 10% by weight of the diluent.

The process may obviously be carried out continuously, additional provision being made for continuous hydrogen feed and for continuous draining of the reaction medium, the phase separation and/or filtration to separate the catalyst from the liquid mixture originating from the reaction zone, the separation of the required product by distillation and, if appropriate, the recycling of at least a proportion of the catalyst and of the diluent which has been made basic, accompanied by a complementary feed of catalyst, diluent and alkali metal or quaternary ammonium hydroxide.

In order to further illustrate the present invention and the advantages thereof, the following specific examples are given, it being understood that same are intended only as illustrative and in nowise limitative. In said examples to follow, the immediately following conventions are adopted:

DC : denotes the degree of conversion of 2-methylglutaronitrile.
CY : denotes the number of moles of product under consideration produced per 100 moles of 2-methylglutaronitrile employed.
mpda : 2-methylpentanediamine.
mpp : methylpiperidine.

Also in said examples to follow, the amounts of Raney nickel which are mentioned therein refer to the solids content.

EXAMPLE 1

The following materials were charged into a stainless steel autoclave, 3.6 liters in capacity, equipped with an anchor stirrer rotating at 240 revolutions/minute and with three counterblades (the reactor design and the stirring efficiency being such that, in consideration of the consumption of hydrogen per unit time, the reaction is never limited by gas transfer into the liquid phase):

(i) 1,060 ml of ethanol containing 4% (by weight) of water;

(ii) 120 g of Raney nickel (Ni 50) marketed by Procatalyse, prepared by alkaline digestion of an alloy of nickel and aluminum containing equal proportions by weight of nickel and aluminum (the alloy being chromium-doped); and (iii) 31 g of sodium hydroxide pellets.

The autoclave, purged with nitrogen, was then pressurized with hydrogen to 15 bars and heated to 100° C. 13.1 moles of 2-methylglutaronitrile (of a purity greater than 99.5%) were then injected over 4 hours. The reaction was continued for approximately 1 hour, 30 minutes, upon completion of such injection, the temperature and pressure conditions being maintained. This period, deemed the finishing period, was the time necessary for the composition of the reaction medium, monitored by gas phase chromatography, to evidence no further change.

At the end of the test, the reaction mixture was cooled and was then filtered. It was then analyzed by gas phase chromatography.

The results obtained were as follows:

| | |
|---|---|
| DC = | 100% |
| CY (mpda) = | 86% |
| CY (mpp) = | 10% |
| CY (other products) = | 4% |

EXAMPLES 2 to 4; Control Test a

A series of tests was carried out under the following common conditions by following the operating procedure described in Example 1:

(a) a 300-ml capacity reactor was employed;

(b) a total of 0.1 mole of 2-methylglutaronitrile was injected;

(c) an exogenous diluent (100 ml) and Raney nickel (Ni 50, defined above), in a proportion of 2.16 g, were employed;

(d) the temperature was 65° C.;

(e) the hydrogen pressure was 15 bars.

The individual conditions and the results obtained are reported in the Table below:

DC=100% in all the tests.

TABLE

| Example No. | Diluent | Basic agent Nature | (g) | Time in min Injection | Finishing | CY (mpda) % |
|---|---|---|---|---|---|---|
| 2 | Absolute ethanol | KOH | 0.58 | 260 | 30 | 89 |
| 3 | Absolute ethanol | NaOH | 0.56 | 130 | 20 | 92 |
| a | Absolute ethanol | NH₄OH | 0.24 | 180 | 30 | 16 |
| 4 | Ethanol containing 4% (wt) of water | NaOH | 0.56 | 180 | 30 | 86 |

EXAMPLE 5 Control Test b

Example 4 above was reproduced with modification to the nature of the diluent and to the reaction temperature, which was now 100° C.

In Example 5, the diluent was anhydrous isopropanol; in Control Test b, the diluent was isopropanol containing 5% by weight of water. The injection time was 90 min, the finishing time 30 min. In both cases DC=100%, but the selectivities were very different:

| | |
|---|---|
| CY (mpda) in Example 5: | 95.5% |
| CY (mpda) in Test b: | 5% |

EXAMPLE 6

The following materials were charged into an autoclave 300 ml in capacity:

(i) 100 ml of 2-methylpentanediamine (diluent);

(ii) 12.9 g of Raney nickel (Ni 50 defined above; and (iii) 0.56 g of sodium hydroxide pellets.

The autoclave, purged with nitrogen, was then pressurized with hydrogen to 15 bars and heated to 100° C. 1.03 mole of 2-methylglutaronitrile was then injected over 3 hours, and the temperature and pressure conditions were maintained for 30 minutes.

The following results were obtained:

| | |
|---|---|
| DC = | 100% |
| CY (mpda) = | 88.1% |

EXAMPLE 7

A test was carried out in an apparatus similar to that described in Examples 2 to 4, on a charge containing:

(i) 0.1 mole of 2-methylglutaronitrile;

(ii) 100 ml of 100% ethanol;

(iii) 2.16 g of Raney nickel (Ni 50 described above); and (iv) 0.58 g of potassium hydroxide pellets.

After 7 hours of contact at 40° C. at 14 bars, the following results were obtained:

| | |
|---|---|
| DC = | 100% |
| CY (mpda) = | 75.9% |

EXAMPLE 8

The following materials were charged into a stainless steel autoclave, 1 l in capacity, heated by means of a jacket, stirred with a 6-blade turbine and equipped with 4 counterblades and purged with nitrogen:

(i) 300 ml of 96% ethanol;

(ii) 33 g of Raney nickel (Ni 50 defined above); and (iii) 1.7 g of a 50% strength aqueous sodium hydroxide solution.

The reactor was pressurized with hydrogen, stirring was commenced at 1,500 rev/min and the temperature was raised to approximately 50° C.

The pressure in the reactor was then adjusted to 5 bars and 2.82 moles of 2-methylglutaronitrile were then introduced over 3 h, 40 min, the temperature being controlled such that it was maintained at 65° C.

The introduction of 2-methylglutaronitrile was then terminated and the temperature and pressure conditions were maintained for 30 min.

DC=100%

CY (mpda)=72.7%, which corresponded to an hourly output of 0.56 mole of 2-methylpentanediamine.

EXAMPLE 9

Example 8 was reproduced with the hydrogen pressure modified; the pressure in the reactor was now maintained at 10 bars.

3.52 moles of 2-methylglutaronitrile were fed over 4 h, 40 min, and the temperature and pressure conditions were maintained for 30 min after the completion of the injection.

The results were as follows:

DC=100%

CY (mpda)=79.7%, which corresponded to an hourly output of 0.6 mole of 2-methylpentanediamine.

While the invention has been described in terms of various preferred embodiments, the skilled artisan will appreciate that various modifications, substitutions, omissions, and changes may be made without departing from the spirit thereof. Accordingly, it is intended that the scope of the present invention be limited solely by the scope of the following claims, including equivalents thereof.

What is claimed is:

1. A process for the preparation of 2-methylpentanediamine, comprising selectively liquid-phase hydrogenating less than about 20% by weight of 2-methylglutaronitrile, initially nonammoniacal basic reaction medium in the presence of a catalytically effective amount of a Raney nickel-based catalyst, at a temperature of from 40° C. to 150° C., at a total pressure of less than 40 bars, and said reaction containing not more than 10% by weight of water.

2. The process as defined by claim 1, said initially nonammoniacal basic reaction medium comprising less than 10% by weight of 2-methylglutaronitrile.

3. The process as defined by claim 1, said initially nonammoniacal basic reaction medium comprising an exogenous diluent.

4. The process as defined by claim 1, said initially nonammoniacal basic reaction medium comprising an endogenous diluent.

5. The process as defined by claim 3, said exogenous diluent comprising an alkanol containing from 1 to 12 carbon atoms.

6. The process as defined by claim 4, said endogenous diluent comprising 2-methylpentanediamine, or 2-methylpentanediamine admixed with 3-methylpiperidine.

7. The process as defined by claim 1, said reaction medium containing no more than 4% by weight of water.

8. The process as defined by claim 1, said temperature ranging from 60° to 110° C.

9. The process as defined by claim 1, said pressure ranging from 5 to 25 bars.

10. The process as defined by claim 1, said initially nonammoniacal basic reaction medium comprising hydroxide in an amount of from 0.5 to 50 molar percent of the nickel which comprises said catalyst.

11. The process as defined by claim 5, said alkanol comprising ethanol or isopropanol.

12. The process as defined by claim 1, said reaction medium being devoid of exogenous diluent and comprising a 2-methylpentanediamine endogenous diluent, optionally admixed with 3-methylpiperidine.

13. The process as defined by claim 1, said reaction medium comprising sodium hydroxide or potassium hydroxide.

14. The process as defined by claim 1, comprising introducing 2-methylglutaronitrile into the reaction medium at a rate such that at any time during the reaction the hydrogen consumption is 4 moles per mole of 2-methylglutaronitrile, ±3%, and the concentration of 2-methylglutaronitrile in said reaction medium is less than 0.1% by weight.

15. The process of claim 1 for the preparation of 2-methylpentanediamine wherein the initially nonammoniacal basic reaction medium comprises sodium hydroxide or potassium hydroxide, said reaction containing not more than 4% by weight of water.

* * * * *